United States Patent [19]

Harsch

[11] 4,039,254

[45] Aug. 2, 1977

[54] ELECTRO-OPTIC WELDING LENS ASSEMBLY USING MULTIPLE LIQUID CRYSTAL LIGHT SHUTTERS AND POLARIZERS

[75] Inventor: Thomas B. Harsch, Stow, Ohio

[73] Assignee: Mack Gordon, Cleveland, Ohio

[21] Appl. No.: 690,554

[22] Filed: May 27, 1976

[51] Int. Cl.² ............................................. G02F 1/13
[52] U.S. Cl. ................................. 350/160 LC; 2/8; 350/150
[58] Field of Search ................ 350/150, 160 LC; 2/8

[56] References Cited

U.S. PATENT DOCUMENTS

| 3,873,804 | 3/1975 | Gordon | 350/160 LC X |
| 3,881,808 | 5/1975 | Gurtler et al. | 350/160 LC |
| 3,937,561 | 2/1976 | Peterson et al. | 350/160 LC X |

*Primary Examiner*—Edward S. Bauer
*Attorney, Agent, or Firm*—Brown, Murray, Flick & Peckham

[57] ABSTRACT

A liquid crystal welding lens assembly for use as the eyepiece of a welding helmet in which the light transmission of the lens assembly is no greater than 0.01% during the existence of a welding arc. This is achieved with the use of at least two liquid crystal light shutters and three polarizers alternately arranged in tandem.

5 Claims, 4 Drawing Figures

U.S. Patent          Aug. 2, 1977          4,039,254
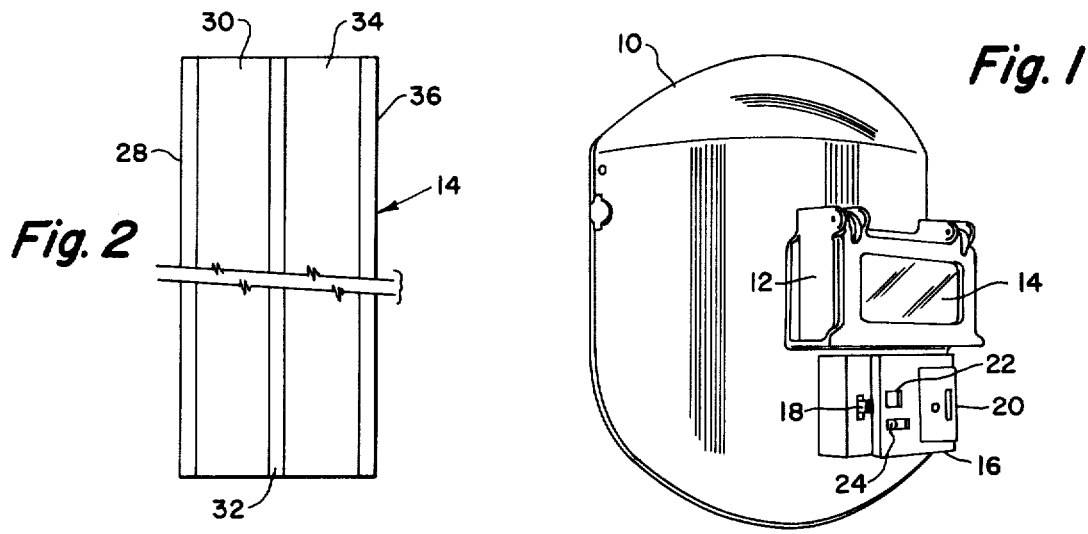
Fig. 1
Fig. 2
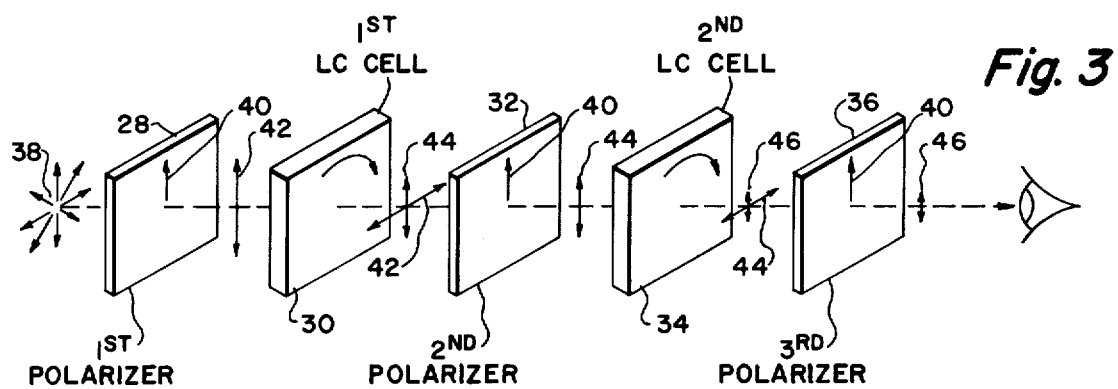
Fig. 3
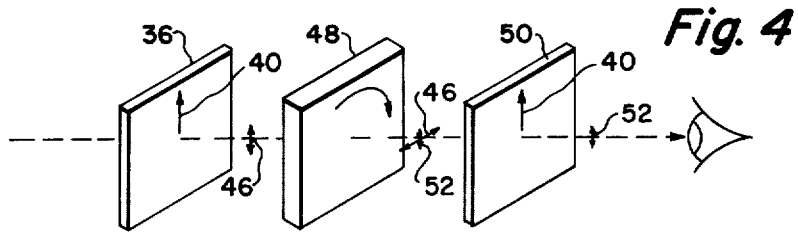
Fig. 4

ELECTRO-OPTIC WELDING LENS ASSEMBLY USING MULTIPLE LIQUID CRYSTAL LIGHT SHUTTERS AND POLARIZERS

BACKGROUND OF THE INVENTION

In U.S. Pat. No. 3,873,804, a welder's helmet is disclosed which uses as a protective lens assembly a liquid crystal light shutter. Such a light shutter comprises a layer of nematic liquid crystal material sandwiched between parallel transparent plates coated on their faces in contact with the liquid crystal material with transparent conductive coatings. By rubbing the transparent conductive coating in contact with the liquid crystal material at right angles to each other, a twisted nematic structure results which will rotate the plane of polarized light through 90°. However, when an electrical field is applied across the liquid crystal material, the plane of polarization will no longer be rotated though 90°. Thus, if crossed polarizers are disposed on opposite sides of the liquid crystal cell and their planes of polarization are parallel to the respective rubbed lines on the transparent coatings, polarized light will normally pass through the cell. However, when an electrical field is applied across the liquid crystal material and the plane of polarization is no longer rotated through 90°, the cell will block light. Alternatively, by using parallel polarizers, the cell will normally be opaque, or substantially opaque, and will become light-transmitting only when an electrical field is applied across the liquid crystal material.

While most applications for flash protection require a light transmission of only 0.01%, a liquid crystal lens assembly of the type described above will achieve a minimum light transmission of about 0.1% due to the fact that the liquid crystal material is a semi-ordered fluid which will scatter and depolarize some of the light passing therethrough.

SUMMARY OF THE INVENTION

In accordance with the present invention, a protective lens assembly incorporating a liquid crystal light shutter is provided for a welding helmet wherein two or more liquid crystal light shutters and at least three polarizers are utilized alternately in tandem to achieve a maximum light transmission of about .01% during the time that a welding arc is struck.

Specifically, there is provided in accordance with the invention a lens assembly for use as the eyepiece of a welding helmet comprising, in series, (1) a first polarizer, (2) a first liquid crystal cell adapted to rotate the plane of polarized light through a 90° angle and responsive to an electric field to no longer rotate the plane of polarized light, (3) a second polarizer oriented parallel to the first polarizer, (4) a second liquid crystal cell also capable of rotating the plane of polarized light through a 90° and responsive to an electric field to no longer rotate the plane of polarization, and (5) a third polarizer oriented parallel to the second polarizer. With no electric field applied across the respective liquid crystal cells, only about 0.01% of the available light will pass through the sandwich structure. On the other hand, when electric fields are applied across both liquid crystal cells simultaneously, the liquid crystal cells will no longer rotate the plane of polarized light through 90°; and about 9% of the visible light will pass through, enabling the welder to view his work under ambient light conditions.

It is also possible to further reduce the amount of light passing through the lens assembly in the presence of a welding arc by adding still a third liquid crystal cell and a fourth polarizer. In this case, only 0.005% of the light will pass through the lens assembly when no electric fields are applied across the liquid crystal cells; while about 6% will pass through when fields are applied. This still enables the welder to view his work under ambient lighting conditions.

The above and other objects and features of the invention will become apparent from the following detailed description taken in connection with the accompanying drawings which form a part of this specification, and in which:

FIG. 1 is a perspective view of a welding helmet incorporating the liquid crystal lens assembly of the invention;

FIG. 2 is a side view of one embodiment of the invention employing two individual liquid crystal cells and three polarizers;

FIG. 3 is an exploded view of one embodiment of the invention employing two individual liquid crystal cells and three polarizers; and FIG. 4 is an exploded view of still another embodiment of the invention employing three liquid crystal cells and four polarizers.

With reference now to the drawings, and particularly to FIG. 1, a welder's helmet 10 is shown provided with a window or lens assembly 12 having an eyepiece 14 comprising a liquid crystal light shutter assembly hereinafter described in greater detail. Beneath the lens assembly 12 is an electronic unit 16 incorporating a manually-operated switch 18 which acts to switch the control system for the lens assembly ON or OFF. The electronic unit 16 is provided with a door or flap 20 which can be opened to insert a battery into the unit. Unit 16 is also preferably provided with two windows 22 and 24. In accordance with the teachings of copending application Ser. No. 674,903, filed Apr. 8, 1976, the control system preferably utilizes two phototransistors and two light filters, one of which will pass visible light only and the other of which will pass infrared wave energy only. These are disposed behind the windows 22 and 24 in the unit 16. By reference to the aforesaid copending application Ser. No. 674,903, it will be seen that the use of two phototransistors, one of which is responsive to visible light and the other to infrared, insures that the lens assembly will not become opaque in the presence of visible light only and at the same time insures that the lens assembly will become light-transmitting even though infrared energy may be emitted from a still-hot weld bead after the welding arc itself is extinguished. It should be understood, however, that the particular control system utilized is unimportant as regards the present invention, just so long as the light shutter assembly, about to be described, becomes substantially opaque (i.e., 0.01 transmission) in the presence of a welding arc and light-transmitting (i.e., at least 6% transmission) when the welding arc is extinguished.

With reference to FIG. 2, an end view of the lens assembly 14 of FIG. 1 is shown. It comprises a sandwich structure including a first polarizer 28, a first nematic liquid crystal cell 30, a second polarizer 32, a second nematic liquid crystal cell 34 and a third polarizer 36. These are shown as an exploded assembly in FIG. 3.

With specific reference to FIG. 3, unpolarized light passing through the lens assembly of FIG. 2 is indicated generally by the reference numeral 38. The directions of polarization of the three polarizers 28, 32 and 36 are indicated by the arrows 40; and it will be noted that the directions of polarization of the three polarizers are parallel. The liquid crystal cells 30 and 34 are of the type shown, for example, in Fergason U.S. Pat. No. 3,918,796. For purposes of the present application, it will suffice to state that such cells comprise a pair of parallel transparent plates having films of transparent conducting material on their facing surfaces. In-between the transparent conducting films is a layer of nematic liquid crystal material. The transparent conducting films are rubbed at right angles to each other such that a twisted nematic structure results in the liquid crystal material which will rotate the plane of plane polarized light by 90°. However, when an electrical field is applied across the liquid crystal material as by connecting the opposite terminals of a battery to the two transparent conducting films, the liquid crystal material will no longer rotate the plane of polarized light.

The orientation of the nematic molecules in the cells 30 and 34 is statistical and dynamic. Consequently, they do not trace out a perfect quarter helix; and the thermal motion in the liquid crystal causes the molecules to fluctuate with time, these fluctuations generally occurring at a rate of 10 to 100 times per second. As a result of these fluctuations, the minimum light transmission achievable with a nematic liquid crystal cell and two polarizers is about 0.1%; whereas most applications for flash protection require a light transmission of about 0.01%. Although the two polarizers used in the nematic liquid crystal light shutter are capable of an extinction of 0.005%, leakage of light occurs due to the aforesaid dynamic fluctuations of the nematic molecules which depolarize a portion of the light from the first polarizer. Since the second polarizer is static and cannot move to follow the molecular fluctuations, a small percentage of light, about 0.1% passes through the cell.

Initially, for purposes of explanation, it will be assumed that electric fields are not applied across the liquid crystal films of the two liquid cells 30 and 34 in FIG. 3 and that the cells will, in fact, rotate the plane of plane polarized light by 90°. The polarizer 28 will pass polarized light having a plane of polarization in the direction of arrow 40 in an amount equal to 38% of the total available light from source 38. This light fraction is indicated by the vector 42. After passing through the first liquid crystal cell 30, and assuming that an electric field is not applied across the liquid crystal therein, most of the polarized light will be rotated through 90° such that the vector 42 is now rotated through 90°. However, 1% of the light, represented by vector 44, will not be rotated due to the dynamic fluctuations explained about and will pass through the second polarizer 32. This 1% portion of the light, represented by vector 44, will now be rotated through 90° by the second liquid crystal cell 34. At the same time, it will pass about 0.01% of the light at right angles thereto, this being represented by the vector 46. Now, light represented by the vector 46 will pass through polarizer 36 to the eye of the welder. On the other hand, if electric fields are applied across the liquid crystal films of the liquid crystal cells 30 and 34, the polarized light will no longer be rotated through 90°; and polarized light represented by the vector 42 and comprising about 32% of the total available light from source 38 will pass through the lens assembly.

In the operation of the assembly of FIG. 1, liquid crystal cells 30 and 34 will normally be connected to a source of power such that the lens assembly will be "driven" to a light-transmitting condition. Only in response to a welding arc detected by the photodetectors hereinbefore described will the potential be removed from across the liquid crystal cells such that only 0.01% of the light will be transmitted during the existence of a welding arc. This insures, for example, that the lens assembly will not become light-transmitting while the arc exists due to a power failure or the like.

In FIG. 4, only the last polarizer 36 is shown; however it is to be assumed that the remaining elements of FIG. 3 are included also in the embodiment of FIG. 4. In this case, however, a third liquid crystal cell 48 and a fourth polarizer 50 are included. The result, of course, is that the liquid crystal cell 48, assuming that no potential is applied across the liquid crystal layer therein, will rotate the vector 46 through 90° such that it cannot pass through the last polarizer 50; and only a vector representing about 0.0005% of the total light from source 38 will pass to the eye of the welder, this being represented by the vector 52.

Although the invention has been shown in connection with certain specific embodiments, it will be readily apparent to those skilled in the art that various changes in form and arrangement of parts may be made to suit requirements without departing from the spirit and scope of the invention.

I claim as my invention:

1. In a welding helmet, a protective welding lens assembly comprising at least two liquid crystal light shutters and at least three polarizers arranged alternately in tandem to achieve a maximum light transmission through the lens assembly of about 0.01%.

2. The protective welding lens assembly of claim 1 wherein said lens assembly comprises, in series, a first polarizer, a first liquid crystal cell adapted to rotate polarized light through a 90° angle, a second polarizer, a second liquid crystal cell adapted to rotate polarized light through a 90° angle, and a third polarizer, all of said polarizers being polarized in the same direction and both of said first and second liquid crystal cells being adapted, in response to an electrical signal, to no longer rotate light through a 90° angle.

3. The protective lens assembly of claim 2 wherein each of said liquid crystal cells comprises a layer of liquid crystal material sandwiched between opposing parallel plates coated over their surfaces facing the liquid crystal layer with transparent electrically-conductive films, said films being pretreated by rubbing the same in parallel lines at right angles to each other whereby the liquid crystal cell will rotate plane polarized light through 90°, and means for applying an electric field between said transparent conductive films and across said liquid crystal material to thereby prevent said liquid crystal cells from rotating plane polarized light through 90°.

4. The combination of claim 2 including a third liquid crystal cell in series with and following said third polarizer, and a fourth polarizer following said third liquid crystal cell.

5. The protective lens assembly of claim 4 wherein said fourth polarizer is polarized parallel to said first, second and third polarizers.

* * * * *